(12) United States Patent
Fiandaca et al.

(10) Patent No.: US 8,795,972 B2
(45) Date of Patent: Aug. 5, 2014

(54) REAGENTS, METHODS AND KITS FOR CLASSIFICATION OF FUNGI AND DIRECTION OF ANTI-FUNGAL THERAPY

(75) Inventors: Mark Fiandaca, Princeton, MA (US); Henrik Stender, Gentofte (DK)

(73) Assignee: AdvanDx, Inc., Woburn, MA (US)

(*) Notice: Subject to any disclaimer, the term of this patent is extended or adjusted under 35 U.S.C. 154(b) by 0 days.

(21) Appl. No.: 12/288,051

(22) Filed: Oct. 15, 2008

(65) Prior Publication Data

US 2009/0092994 A1 Apr. 9, 2009

Related U.S. Application Data

(63) Continuation of application No. 11/524,988, filed on Sep. 20, 2006, now abandoned.

(60) Provisional application No. 60/719,153, filed on Sep. 20, 2005, provisional application No. 60/789,656, filed on Apr. 5, 2006.

(51) Int. Cl.
*C12Q 1/68* (2006.01)
*C07H 21/04* (2006.01)

(52) U.S. Cl.
USPC .......................................... 435/6.13; 536/24.3

(58) Field of Classification Search
None
See application file for complete search history.

(56) References Cited

U.S. PATENT DOCUMENTS

| 5,539,082 | A | * | 7/1996 | Nielsen et al. ................ 530/300 |
| 5,541,308 | A | * | 7/1996 | Hogan et al. ................ 536/23.1 |
| 2002/0098483 | A1 | | 7/2002 | Loffler et al. |
| 2003/0175727 | A1 | | 9/2003 | Hyldig-Nielsen et al. |
| 2004/0002592 | A1 | | 1/2004 | Einsele et al. |

FOREIGN PATENT DOCUMENTS

| EP | 0422869 A2 | 4/1991 |
| JP | 03-206900 A | 10/1991 |
| JP | 2000-516100 A | 12/2000 |
| WO | WO-00/73499 | 12/2000 |
| WO | WO-2005/054516 | 6/2005 |

OTHER PUBLICATIONS

Haynes et al ( Journal of Medical Microbiology (1996) vol. 44, pp. 390-396).*
GenBank Accession Z48341.1 GI:671837 (Sep. 2, 1996).*
Ahern et al (The Scientist (1995) vol. 9 p. 1-7).*
Li et al (Analytical Chemistry (2003) vol. 75, pp. 1664-1670).*
Bustin et al (Journal of Molecular endocrinology (2002) vol. 29, pp. 23-39).*
Perry-O'Keefe (Journal of microbial methods (2001) vol. 47, pp. 281-292).*
Rigby, S. Journal of Clinical Microbioloby Jun. 2002, vol. 40, No. 6, pp. 2182-2186.
Stender, H. Applied and Environmental Microbiolgy, Feb. 2001, vol. 67, No. 2, pp. 938-941.
Pfaller, M.A. Diagnosic Microbiolby and Infectious Disease 48 (2004), pp. 201-205.
Shin J H et al: "Rapid Identification of Up to Three Candida Species in a Single Reactino Tube by a 5' Exonuclease Assay Using Fluorescent DNA Probes" Journal of Clinical Microbiology, Washington, DC, US, vol. 37, No. 1, Jan. 1, 1999, pp. 165-170.
Pfaller M A et al: "International surveillance of bloodstream infections due to Candida species: Frequency of occurrence and in vitro susceptibilities to fluconazole, ravuconazole, and voriconazole of isolates collected from 1997 through 1999 in the SENTRY antimicrobial surveillance program" Journal of Clinical Microbiology, vol. 39, No. 9, Sep. 2001, pp. 3254-3259.
Yang Y-L et al: "Susceptibilites to amphotericin B and fluoazole of Candida species in TSARY 2002" Diagnostic Microbiology and Infectious Diseases, Elsevier Science Publishing Co., Amsterdam, NL, vol. 51, No. 3, Mar. 1, 2005, pp. 179-183.
Loeffler J et al: "Rapid detection of point mutations by fluorescence resonace energy transfer and probe melting curves in Candida species" Clinical Chemistry, American Associate for Clinical Chemistry, Washington, DC, vol. 46, No. 5, Jan 1, 2000 pp. 631-635.
Arthington-Skaggs, B.A. et al., "Comparison of Visual and Spectrophotometric Methods of B roth Microdilution MIC End Point Determination and Evaluation of a Sterol Quantitation Method for In Vitro Susceptibility Testing of Fluconazole and Itraconazole against Trailing and Nontrailing *Candida* Isolates", Antimicrobial Agents and Chemotherapy, Aug. 2002, p. 2477-2481.
Haynes, K., "*C.glabrata* gene for large subunit of ribosomal RNA (V3 region)", www.ncbi.nlm.nih.gov, 2012.
Oliveira, et al., "Differentiation of *Candida albicans* and *Candida dubliniensis* by Fluorescent In Situ Hybridization with Peptide Nucleic Acid Probes", J. Clin. Microbiol., Nov. 2001, p. 4138-4141.
Pfaller, M. A. et al., "International Surveillance of Bloodstream Infections Due to *Candida* Species: Frequency of Occurrence and Antifungal Susceptibilities of Isolates Collected in 1997 in the United States, Canada, and South America for the SENTRY Program", J. Clin. Microbiol., Jul. 1998, p. 1886-1889.
Wilson, D.A. et al, "Multicenter Evaluation of a *Candida albicans* Peptide Nucleic Acid Fluorescent In Situ Hybridization Probe for Characterization of Yeast Isolates from Blood Cultures", J. Clin. Microbiol., Jun. 2005, p. 2909-2912.
Evertsson et al., "Detection and identification of fungi in blood using broad-range 28S rDNA PCR amplification and species-specific hybridisation," *APMIS*, 108:385-392 (2000).
Hancock and Dover, "Molecular Coevolution among Cryptically Simple Expansion Segments of Eukaryotic 26S/28S rRNAs," *Mol. Biol. Evol.*, 5(4):377-391 (1988).

* cited by examiner

*Primary Examiner* — Steven Pohnert
(74) *Attorney, Agent, or Firm* — McCarter & English, LLP; Jonathan M. Sparks; Jin Wang, Esq.

(57) ABSTRACT

Provided herein are methods, kits and compositions to classify fungi. Methods are provided for classification of fungi according to established phenotypes, for example, antimicrobial susceptibility profiles. More specifically, the invention provides methods for the use of PNA probes in diagnostic applications, which will aid in the direction of appropriate therapy against fungi.

12 Claims, No Drawings

SEQUENCE LISTING

```
<160> NUMBER OF SEQ ID NOS: 24

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
agagagcagc atgca                                                         15

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gcaaggggcg caaa                                                          14

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aggcaagggg cgca                                                          14

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
agaggcaagg ggcg                                                          14

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
agaggcaagg ggc                                                           13
```

```
<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gcagcggtgc gcaa                                                       14

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
agaggcagcg gtgcg                                                      15

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gagtaacata caaaat                                                     16

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gagagtaaca tacaa                                                      15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gagagagtaa catac                                                      15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
agagagtaac ataca                                                      15
```

```
<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cgagagagta acata                                                          15

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gagagagtaa cataca                                                         16

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aagaagtaac ataca                                                          15

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cccacgagag gca                                                            13

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
acgagaggca agg                                                            13

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
acagtcccaa agtggt                                                         16

<210> SEQ ID NO 18
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
agaactgaca ccctcg                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ccttccacac agactc                                                    16

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
taggtctggg acatc                                                     15

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ccaacgcaat tctcct                                                    16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ctaggttttt tccggc                                                    16

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gcatcaacgc aggct                                                     15

<210> SEQ ID NO 24
<211> LENGTH: 14
```

-continued

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gactcagacc acga                                                        14
```

REAGENTS, METHODS AND KITS FOR CLASSIFICATION OF FUNGI AND DIRECTION OF ANTI-FUNGAL THERAPY

RELATED APPLICATIONS

This application is a continuation of U.S. application Ser. No. 11/524,988, filed Sep. 20, 2006, which claims the benefit of U.S. Provisional Application Ser. No. 60/719,153, filed Sep. 20, 2005 and U.S. Provisional Application Ser. No. 60/789,656, filed Apr. 5, 2006. The contents of each of the aforementioned Applications is hereby incorporated by reference in its entirety herein.

BACKGROUND

Fungal infections, particularly those caused by yeasts, are associated with high morbidity and mortality. An increase in the prevalence of nosocomial fungal infections, especially bloodstream infections (BSI) attributed to *Candida* species, has contributed to an overall increase in the proportion of BSI caused by yeast (Wisplinghoff CID 2004).

The susceptibility of the various *Candida* species to available antifungal compounds is constantly being reexamined and results are widely published. The susceptibility of an isolate to a drug is often described in minimum inhibitory concentration units (MIC) which are often defined in terms of the species as a whole, though susceptibilities can vary widely between isolates of a given species. Measurement of MIC values requires isolation of an organism from a clinical sample followed by exposure of the organism to a drug and subsequent measurement of inhibition (reduction in growth). The US National Committee for Clinical Laboratory Standards (NCCLS) guidelines attempt to standardize these techniques and establish so called "breakpoints" differentiating resistant from non-resistant isolates. In general terms, species are described as resistant to a particular drug when a significant proportion of isolates tested have MIC values greater than the breakpoint, or when the recommended dosage of a drug is found to result in failure of treatment in a significant number of cases. Organisms which demonstrate intermediate susceptibilities are described as "susceptible, dose-de pendant".

Though the susceptibility of a given species to a particular drug can be highly variable between isolates, and patient populations, the established susceptibility of a species is perceived as a good therapeutic guide. In fact, current guidelines from the Infectious Disease Society of America recommend selection of antifungal therapy based on species identification. Antifungal drugs are approved for, and directed towards the treatment of particular *Candida* species, however; identification to a species level is not commonly performed rapidly enough to inform initial therapeutic decisions. Treatment of patients with antifungal drugs is therefore often performed prophylactically, without diagnostic information, or empirically based on preliminary diagnostic information; whereas, selection of optimal therapy must await laboratory identification which may take several days by conventional methods.

*Candida albicans, Candida parapsilosis, Candida tropicalis, Candida glabrata*, and *Candida krusei* account for greater than 95% of yeast isolates from blood (Pfaller JCM, Vol. 39, No. 9. p. 3254-3259) and greater than 97% of nosocomial fungal infections (Wisplinghoff CID 2004). A trend in the relative proportions of these high prevalence *Candida* species has shifted towards a higher incidence of the "drug resistant" species *C. glabrata* and *C. krusei* in some patient populations (Trick et al CID 1998). It has been suggested that this change in species proportion reflects a selection of resistant nosocomial strains through the over use of empiric antibiotics.

The development of antifungal therapy is focused on broad spectrum drugs to reduce the dependence on laboratory identification; however, broad spectrum antifungal drugs may be expensive or associated with adverse side effects. For the antifungal compound, fluconazole, the five most clinically prevalent *Candida* species are generally regarded to fall in three categories. *C. albicans* and *C. parapsilosis* are fluconazole sensitive, *C. tropicalis* has dose-dependent sensitivity to fluconazole, and *C. glabrata* with high prevalence of fluconazole resistance and *C. krusei* which is considered fluconazole resistant. Thus, it is generally accepted that infections of *C. albicans* or *C. parapsilosis* can be treated with a normal regime of fluconazole. Fungal infections caused by *C. tropicalis* can be treated with either an increased dose of fluconazole, or a stronger antifungal drug. *C. glabrata* and *C. krusei* infections are generally treated with caspofungin, voriconazole, amphotericin B, or other strong antifungal compounds.

It would therefore be advantageous to have laboratory tools where the results could be used to select optimal antifungal therapy without having to identify the yeast at the species level.

SUMMARY OF THE INVENTION

Described herein are reagents, methods and kits to identify and categorize fungi according to their established susceptibilities to antifungal agents. Embodiments of the invention utilize probes targeted toward fungal species in such a way that optimal therapy can be selected without necessitating identification of the organisms at the species level. By short-cutting the traditional approach where optimal selection of therapy is awaiting species identification, information for selection of therapy is available faster without compromising the quality of the information. In addition, the invention circumvents the need for separating fungi which require the same treatment hereby simplifying both the analysis and the result interpretation.

The methods and reagents provide information for the direction of therapy for treatment of fungal infections in a rapid and simple manner.

In one embodiment, the invention provides reagents and methods for selection of therapy against clinically prevalent *Candida* species.

In another embodiment the invention provides PNA probes and probe sets targeted toward fungal species such that appropriate therapy can be selected without necessitating identification of the organisms to the species level.

In one embodiment of the invention, the test can provide therapeutic guidance for at least about 70% of yeast species associated with fungemia.

In one embodiment of the invention, a single 2-color, multiplex test can provide therapeutic guidance for at least about 70-85% of yeast species associated with fungemia.

In one embodiment of the invention, a single 3-color, multiplex test provides therapeutic guidance for at least about 95% of yeast species associated with fungemia.

Alternatively, the reagents may be used in an array format rather than a multicolor format where the position of the signal, rather than the color of the signal, provides therapeutic guidance.

In some instances, the therapeutic guidance is for selection of a certain antifungal drug whereas in other instances the guidance is for avoiding certain antifungal drugs. Also, the guidance may be related to the dosing of a certain drug.

It is within the embodiment of this invention to use the probes, methods, and kits provided for guidance in the selection of anti-fungal drugs. Embodiments of the invention can provide information which is particularly useful when choosing between fluconazole and other anti-fungal drugs.

In some instances, absence of a signal by a particular test method provides useful diagnostic information, given that appropriate controls demonstrated that the method was capable of producing a positive result.

In one aspect, provided herein are reagents for the classification of fungi, comprising a probe set complementary to nucleic acid sequences of at least one fungal drug susceptibility-type.

In one embodiment, the reagent further comprises one or more additional probe sets complementary to nucleic acid sequences of other fungi of other drug susceptibility-types.

In another embodiment, the probe sets comprise one or more of nucleic acid probes, locked nucleic acid probes, peptide nucleic acid probes, or other nucleic acid probe mimics or analogues.

In one embodiment, a fungal drug-susceptibility type comprises a full spectrum of response to a compound, wherein the full spectrum of response comprises one or more of susceptible; susceptible/intermediate; intermediate; susceptible/susceptible, dose-dependant; susceptible, dose-dependant; susceptible, dose-dependant/resistent; susceptible-dose/delivery dependent; intermediately resistant; or resistant.

In another embodiment, the fungal drug susceptibility-type comprises resistance to an anti-fungal compound, or combination of compounds.

In another embodiment, the anti-fungal compound or combination of compounds comprises one or more of fluconazole, caspofungin, voriconazole, and amphotericin B.

In one embodiment, at least one fungal drug susceptibility type comprises one or more of a fluconazole-sensitive drug susceptibility-type; a fluconazole-sensitive, dose dependant drug susceptibility-type; or a fluconazole-resistant drug susceptibility-type.

In another embodiment, the fluconazole-sensitive drug susceptibility-type comprises one or more of *Candida albicans* and/or *Candida parapsilosis*.

In one embodiment, the fluconazole-sensitive, dose dependant drug susceptibility-type comprises *Candida tropicalis*.

In one embodiment, the fluconazole-resistant drug susceptibility-type comprises one or more of *Candida glabrata* or *Candida krusei*.

In another embodiment, the fungi comprise caspofungin-, voriconazole- or amphotericin B-sensitive.

In one embodiment, the nucleic acid sequences comprise one or more of ribosomal RNA (including, but not limited to 5.8S, 18S and 26S sequences), ribosomal DNA, (including, but not limited to 5.8S, 18S and 26S sequences) or complements thereof.

In another embodiment, at least a portion of a probe of the probe set is at least about 86% identical to the nucleobase sequence or complement thereof selected from SEQ. ID NOS 1-24.

In one embodiment, the probe sequences comprise 8-17 subunits in length.

In one embodiment, the probe set comprises at least one detectable moiety.

In another embodiment, the detectable moiety or moieties comprise one or more of a conjugate, a branched detection system, a chromophore, a fluorophore, a spin label, a radioisotope, an enzyme, a hapten, an acridinium ester or a luminescent compound.

In one embodiment, at least one probe is self-reporting.

In one embodiment, the self-reporting probe comprises a PNA Linear Beacon.

In another embodiment, at least one probe of the probe set is unlabeled.

In one embodiment, at least one probe of the probe set is bound to a support.

In one embodiment, at least one probe of the probe set further comprises a spacer or a linker.

In one embodiment, in situ hybridization is used to analyze a sample for the presence of fungi.

In another embodiment, at least two probes are differently labeled and wherein the probes are adapted to distinguish two or more drug susceptibility-types.

In one embodiment, coincidental fluorescence is used to detect a fungal susceptibility-type.

In another embodiment, the probe set comprises a PNA probe for fluconazole-sensitive fungi and a PNA probe for fluconazole-resistant fungi.

In one embodiment, the fluconazole-sensitive fungi comprise one or more of *C. albicans* or *C. parapsilosis* and wherein the fluconazole-resistant fungi comprise one or more of *C. krusei* or *C. glabrata*

In another embodiment, the probe set comprises one or more of a PNA probe for fluconazole-sensitive fungi, a PNA probe for fluconazole-sensitive/dose-dependant fungi or a PNA probe for fluconazole-resistant fungi.

In one embodiment, the fluconazole-sensitive fungi comprise one or more of *C. albicans* or *C. parapsilosis*, the fluconazole-sensitive/dose dependant fungi comprise one or more of *C. tropicalis* and the fluconazole-resistant fungi comprise one or more of *C. krusei* or *C. glabrata*

In one embodiment, three or more differently labeled probe sets are used to distinguish between antifungal drugs.

According to one aspect, provided herein are methods for determining the susceptibility-type of fungi, comprising contacting a sample with one or more probe sets, wherein the probe set comprises a complementary sequence to a nucleic acid sequence of at least one fungal drug susceptibility-type, and correlating hybridization of a probe to an established susceptibility-type.

In one embodiment, the hybridization is indicative of presence, identity and/or amount of microorganisms in the sample.

In another embodiment, the probe sets comprise an azole sensitivity probe set and an azole resistance probe set.

According to one aspect, provided herein are methods for selecting antifungal therapy, comprising: a) contacting a sample with a probe set, wherein the probe set comprises a complementary sequence to a nucleic acid sequence of at least one fungal drug susceptibility-type; b) hybridizing the probe set to a nucleic acid sample; and c) detecting hybridization; and d) selecting antifungal therapy based on hybridization, if any.

According to one aspect, provided herein are methods for classifying fungi by therapy comprising a) contacting a sample with a probe set, wherein the probe set comprises a complementary sequence to a nucleic acid sequence of at least one fungal drug susceptibility-type; b) hybridizing the probe set to a nucleic acid sample; and c) detecting hybridization; and d) classifying the fungi based on hybridization.

According to one aspect, provided herein are methods to select antifungal therapy, comprising a) contacting a sample with at least two probe sets, wherein the probe sets comprises complementary sequences to a nucleic acid sequences of at least one fungal drug susceptibility-type; b) hybridizing the probe set to a nucleic acid sample; and c) detecting hybridization; and d) selecting antifungal therapy based on hybridization, if any.

In one embodiment, the probe sets comprise one or more of a PNA probe set targeting *C. albicans* and *C. parapsilosis*, a PNA probe set targeting *C. tropicalis*, and a PNA probe set targeting *C. glabrata* and *C. krusei*, wherein the PNA probe sets are independently labeled and wherein detection of hybridization of one or more of the PNA probes targeting *C. albicans* and *C. parapsilosis* indicates selection of fluconazole, detection of hybridization of one or more of the PNA probes targeting *C. tropicalis* indicates selection of increased dose of fluconazole and wherein detection of hybridization of one or more PNA probes targeting *C. glabrata* and *C. krusei* indicates selection of caspofungin, voriconazole, or amphotericin B.

In another embodiment, the analysis is in situ.

In another embodiment, the analysis comprises fluorescence in situ hybridization.

In another embodiment, the probes or their complementary sequences have been synthesized or amplified in a reaction.

In one embodiment, results are generated in less than 8 hours.

In one embodiment, results are generated in less than 3 hours.

In another embodiment, nucleic acid synthesis or nucleic acid amplification reactions are selected from the group consisting of: Polymerase Chain Reaction (PCR), Ligase Chain Reaction (LCR), Strand Displacement Amplification (SDA), Transcription-Mediated Amplification (TMA), Rolling Circle Amplification (RCA) and Q beta replicase.

In one embodiment, the method further comprises adding at least one blocking probe to reduce or eliminate hybridization of the probe to a non-target sequence.

In another embodiment, the nucleic acid sample is immobilized to a surface.

In another embodiment, at least one probe of at least one probe set is immobilized to a surface.

In another embodiment, the at least one probe is a component of an array.

In another embodiment, the probe set comprises one or more of the PNA probe sets described herein.

In another embodiment, the sample is a biological sample.

In another embodiment, the biological sample is blood, urine, secretion, sweat, sputum, stool, mucous, or cultures thereof.

According to one aspect, provided herein are kits for selecting antifungal therapy, comprising a) probe set comprising a complementary sequence to a nucleic acid sequence of at least one fungal drug susceptibility-type and b) other reagents or compositions necessary to perform the assay.

In one embodiment, the kit is used in an in situ hybridization assay. In another embodiment, the kit is used for a real-time PCR assay.

In one embodiment, the kit is used to examine clinical samples or cultures thereof.

Specific PNA probes, kits and methods are provided.
Generic PNA probes, kits and methods are provided.

DETAILED DESCRIPTION OF THE INVENTION

Provided herein are methods for detection of nucleic acid targets which confer azole resistance to fungi. A multitude of molecular diagnostic methods are available for detection and identification of organisms involved in infectious disease. Amplification techniques, particularly those using the polymerase chain reaction (PCR) have been described for species identification for a wide range of bacteria and fungi. Amplification methods, probes and primers for detection of nucleic acid targets indicative of the presence of various fungi are described in several places (U.S. Pat. No. 6,858,387, US2003186259, U.S. Pat. No. 6,235,890). In addition, amplification methods have been described for detection of genes involved in antifungal resistance, see US2004185478.

A detection method which correlates to therapy has also been described (see US2002098483, incorporated herein by reference), through detection of nucleic acid targets (genes) which confer resistance to particular drug types.

Peptide nucleic acid probes, PNA, are useful tools for detection and analysis of microorganisms, particularly when they are applied in fluorescence in situ hybridization assays (FISH) (Stender, JMicro Meth 48, 2001). PNA FISH assays are commercially available for rapid detection of organisms to a species level. PNA probes have been described elsewhere for detection of *Candida* species (see US2003175727 incorporated herein by reference), however, as with all other methods for species identification, the time and complexity required for identification of *Candida* yeast to species often prevents immediate selection of the most appropriate therapy. Likewise, ChromAgar is a novel, simple method which enables species identification of most clinically relevant species in a single test; however, it can take several days to get a result.

Besides facilitating faster and better selection of appropriate therapy, the tools described herein could also be used to select safe, narrow spectrum, and high potency antifungal drugs that are often not selected due to the time constraints imposed by current speciation methods and susceptibility testing methods.

1. DEFINITIONS a. As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

b. As used herein, the term "nucleobase sequence" means any segment of a polymer that comprises nucleobase-containing subunits. Non-limiting examples of suitable polymers or polymer segments include oligodeoxynucleotides, oligoribonucleotides, peptide nucleic acids, nucleic acid analogs, nucleic acid mimics, and/or chimeras.

c. As used herein, the term "target sequence" means the nucleobase sequence that is to be detected in an assay.

d. As used herein, the term "probe" means a polymer (e.g., a DNA, RNA, PNA, chimera or linked polymer) having a probing nucleobase sequence that is designed to sequence-specifically hybridize to a target sequence of a target molecule of an organism of interest.

e. As used herein, "analyze" means that the individual bacteria are marked for detection, identification and/or quantitation and/or for determination of resistance to antibiotics (antimicrobial susceptibility).

f. As used herein, the term "peptide nucleic acid" or "PNA" means any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610, 5,986,053, 6,107,470 and 6,357,163. In the most preferred embodiment, a PNA subunit consists of a naturally occurring or non-naturally occurring nucleobase attached to the aza nitrogen of the N-[2-(aminoethyl)] glycine backbone through a methylene carbonyl linkage.

g. As used herein, the term "locked nucleic acid" or "LNA" means any oligomer, linked polymer or chimeric oligomer, comprising one or more LNA subunits (residues), including any of the polymers referred to or claimed as locked nucleic acids, and nucleic acid analogs in U.S. Pat. Nos. 6,639,059, 6,670,461, United States Patent Application numbers US2003077609, US2003224377, US2003082807 and World Patent Office Document number WO03095467. In the most preferred embodiment, a LNA subunit consists of a naturally occurring or non-naturally occurring ribonucleoside in which the 4' oxygen is joined to the 2' carbon through a methylene linkage.

h. As used herein, the terms "label" and "detectable moiety" are interchangeable and shall refer to moieties that can be attached to a probe to thereby render the probe detectable by an instrument or method.

i. As used herein the term "established phenotypes" is used to describe features of an organism which have been observed or measured and published by the scientific or medical community, and are generally understood to be a characteristic of the organism.

j. As used herein the term "susceptibility-type", or "drug susceptibility-type", is used to indicate the level of response that an infectious organism of a particular type has demonstrated in the past to exposure to a drug. Such levels of response range from no response to a very strong response, and include, but are not limited to "susceptible", "susceptible/ intermediate", "intermediate", "susceptible/susceptible, dose-dependant", "susceptible, dose-dependant", "susceptible, dose-dependant/resistant", "susceptible-dose/delivery dependent", "intermediately resistant", and "resistant". Synonymic descriptions of the listed levels of response are also included.

Some examples of drugs that may be indicated in this context are fluconazole, caspofungin, voriconazole, amphotericin B, or other anti-fungal drug or drugs. For example, an infectious organism which is resistant to the normal therapeutic dose of fluconazole belongs in the "resistant" susceptibility-type for fluconazole.

A collaborative effort between The US Food and Drug Administration and the Pharmaceutical Research Manufacturers Association published a Target Product Information document in the year 2000 to provide a template for the drug development process. In this document, guidelines are offered for interpretation of the code of regulations governing the labeling of pharmaceutical products (21 CFR 201). Guidelines for 21 CFR 201.56, section b "Clinical Pharmacology" give the following definitions. We incorporate these published definitions only as examples.

A report of "susceptible" indicates that the pathogen is likely to be inhibited if the antimicrobial compound in blood reaches the concentrations usually achievable. A report of "intermediate" indicates that the result should be considered equivocal, and, if the microorganism is not fully susceptible to alternative, clinically feasible drugs, the test should be repeated. This category implies possible clinical applicability in body sites where the drug is physiologically concentrated or in situations where high dosage of drug can be used. This category also provides a buffer zone which prevents small uncontrolled technical factors from causing major discrepancies in interpretation. A report of "resistant" indicates that the pathogen is not likely to be inhibited if the antimicrobial compound in the blood reaches the concentrations usually achievable; other therapy should be selected.

Drug susceptibility-type is assessed based on an expected result, which is derived from historical, empirical or experimental evidence.

k. As use herein, the term "anti-fungal drug" is used to include any compound or mixture of compounds used in a pharmaceutical way to effect the growth, viability, or propagation of a fungus, or suspected fungus. Examples of such compounds include but are not limited to fluconazole, caspofungin, caspofungin acetate, voriconazole, amphotericin B, amphotericin B liposomal, itraconazole, flucytosine, candins, posaconazole, ravuconazole, polyenes, azoles, allylamines, and derivatives, or combinations thereof.

l. As used herein, the term "coincidental fluorescence" is used to describe the perception of a color which is generated by the simultaneous detection of light emissions of two or more labels located near enough in space so as to be irresolvable. The detection of coincidental fluorescence can be either by eye or a photon-sensitive device.

2. DESCRIPTION

I. General:
PNA Synthesis:
Methods for the chemical assembly of PNAs are well known (see: U.S. Pat. Nos. 5,539,082, 5,527,675, 5,623,049, 5,714,331, 5,736,336, 5,773,571, 5,786,461, 5,837, 459, 5,891,625, 5,972,610, 5,986,053 and 6,107,470).
PNA Labeling:
Preferred non-limiting methods for labeling PNAs are described in U.S. Pat. Nos. 6,110,676, 6,361,942, 6, 355,421, the examples section of this specification or are otherwise well known in the art of PNA synthesis and peptide synthesis.
LNA Synthesis:
Methods for the chemical assembly of LNAs are well known (see: Patent Nos. US2003077609, US2003224377, US2003082807 and World Patent Office Document number WO03095467)
LNA Labeling:
Preferred non-limiting methods for labeling LNAs are described in U.S. Pat. Nos. 6,639,059, 6,670,461, United States Patent Application numbers US2003077609, US2003224377, US2003082807 and World Patent Office Document number WO03095467 or are otherwise well known in the art of LNA synthesis.
Labels:
Non-limiting examples of detectable moieties (labels) suitable for labeling PNA probes used in the practice of this invention would include a dextran conjugate, a branched nucleic acid detection system, a chromophore, a fluorophore, a spin label, a radioisotope, an enzyme, a hapten, an acridinium ester and a chemiluminescent compound.

Other suitable labeling reagents and preferred methods of attachment would be recognized by those of ordinary skill in the art of PNA, LNA, peptide or nucleic acid synthesis.

Preferred haptens include 5 (6)-carboxyfluorescein, 2,4-dinitrophenyl, digoxigenin, and biotin.

Preferred fluorochromes (fluorophores) include 5 (6)-carboxyfluorescein (Flu), 6-((7-amino-4-methylcoumarin-3-acetyl)amino) hexanoic acid (Cou), 5 (and 6)-carboxy-X—rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), JOE, Tamara or the Alexa dye series (Molecular Probes, Eugene, Oreg.).

Preferred enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Unlabeled Probes:

The probes that are used for the practice of this invention need not be labeled with a detectable moiety to be operable within the methods of this invention, for example when attached to a solid support Self-Indicating Probes:

Beacon probes are examples of self-indicating probes which include a donor moiety and a acceptor moiety. The donor and acceptor moieties operate such that the acceptor moieties accept energy transferred from the donor moieties or otherwise quench signal from the donor moiety. Though the previously listed fluorophores (with suitable spectral properties) might also operate as energy transfer acceptors, preferably, the acceptor moiety is a quencher moiety. Preferably, the quencher moiety is a non-fluorescent aromatic or heteroaromatic moiety. The preferred quencher moiety is 4-((-4-(dimethylamino)phenyl)azo)benzoic acid (dabcyl). In a preferred embodiment, the self-indicating Beacon probe is a PNA Linear Beacon as more fully described in U.S. Pat. No. 6,485,901.

In another embodiment, the self-indicating probes of this invention are of the type described in WIPO patent application WO97/45539. These self-indicating probes differ as compared with Beacon probes primarily in that the reporter must interact with the nucleic acid to produce signal.

Spacer/Linker Moieties:

Generally, spacers are used to minimize the adverse effects that bulky labeling reagents might have on hybridization properties of probes. Preferred spacer/linker moieties for the nucleobase polymers of this invention consist of one or more aminoalkyl carboxylic acids (e.g. aminocaproic acid), the side chain of an amino acid (e.g. the side chain of lysine or ornithine), natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane).

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target sequence combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid sequences are to the target sequence, the more carefully stringency must be controlled. Blocking probes may also be used as a means to improve discrimination beyond the limits possible by optimization of stringency factors. Suitable hybridization conditions will thus comprise conditions under which the desired degree of discrimination is achieved such that an assay generates an accurate (within the tolerance desired for the assay) and reproducible result.

Aided by no more than routine experimentation and the disclosure provided herein, those of skill in the art will easily be able to determine suitable hybridization conditions for performing assays utilizing the methods and compositions described herein. Suitable in-situ hybridization or PCR conditions comprise conditions suitable for performing an in-situ hybridization or PCR procedure. Thus, suitable in-situ hybridization or PCR conditions will become apparent to those of skill in the art using the disclosure provided herein, with or without additional routine experimentation.

Blocking Probes:

Blocking probes are nucleic acid or non-nucleic acid probes that can be used to suppress the binding of the probing nucleobase sequence of the probing polymer to a non-target sequence. Preferred blocking probes are PNA probes (see: U.S. Pat. No. 6,110,676). It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the probes to a non-target sequence that might be present and interfere with the performance of the assay. Blocking probes are particularly advantageous for discrimination to the phylogenetically closest related species.

Probe Sets:

Probe sets of this invention comprise one or more probes. In one embodiment, one or more of the PNA probes of the set can be blocking probes. Probes sets may include any group of one or more of the probes of this invention, whether labeled or non-labeled, and may also include probes not specifically described here, but which include at least one of the probes of this invention. Preferred probe of the invention are listed in Table 1.

TABLE 1

| Sequence ID | Name | Nucleobase sequence |
|---|---|---|
| SEQ ID NO: 1 | Probe A | AGA-GAG-CAG-CAT-GCA |
| SEQ ID NO: 2 | Probe B | GCA-AGG-GGC-GCA-AA |
| SEQ ID NO: 3 | Probe C | AGG-CAA-GGG-GCG-CA |
| SEQ ID NO: 4 | Probe D | AGA-GGC-AAG-GGG-CG |
| SEQ ID NO: 5 | Probe E | AGA-GGC-AAG-GGG-C |
| SEQ ID NO: 6 | Probe F | GCA-GCG-GTG-CGC-AA |
| SEQ ID NO: 7 | Probe G | AGA-GGC-AGC-GGT-GCG |
| SEQ ID NO: 8 | Probe H | GAG-TAA-CAT-ACA-AAA-T |
| SEQ ID NO: 9 | Probe I | GAG-AGT-AAC-ATA-CAA |
| SEQ ID NO: 10 | Probe J | GAG-AGA-GTA-ACA-TAC |
| SEQ ID NO: 11 | Probe K | AGA-GAG-TAA-CAT-ACA |
| SEQ ID NO: 12 | Probe L | CGA-GAG-AGT-AAC-ATA |
| SEQ ID NO: 13 | Probe M | GAG-AGA-GTA-ACA-TAC-A |

TABLE 1-continued

| Sequence ID | Name | Nucleobase sequence |
|---|---|---|
| SEQ ID NO: 14 | Probe N | AAG-AAG-TAA-CAT-ACA |
| SEQ ID NO: 15 | Probe O | CCC-ACG-AGA-GGC-A |
| SEQ ID NO: 16 | Probe P | ACG-AGA-GGC-AAG-G |
| SEQ ID NO: 17 | Probe Q | ACA-GTC-CCA-AAG-TGG-T |
| SEQ ID NO: 18 | Probe R | AGA-ACT-GAC-ACC-CTC-G |
| SEQ ID NO: 19 | Probe S | CCT-TCC-ACA-CAG-ACT-C |
| SEQ ID NO: 20 | Probe T | TAG-GTC-TGG-GAC-ATC |
| SEQ ID NO: 21 | Probe U | CCA-ACG-CAA-TTC-TCC-T |
| SEQ ID NO: 22 | Probe V | CTA-GGT-TTT-TTC-CGG-C |
| SEQ ID NO: 23 | Probe W | GCA-TCA-ACG-CAG-GCT |
| SEQ ID NO: 24 | Probe X | GAC-TCA-GAC-CAC-GA |

Table 1 displays preferred probes of the invention. With reference to Table 1, the column on the left displays the sequence identification number, the center column displays the probe name, and the column on the right displays the nucleobase sequence of the probe.

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the PNA probe is to be used. The preferred PNA probes of this invention are labeled with one or more detectable moieties selected from the group consisting of fluorophores, enzymes and haptens.

In preferred embodiments, the probes of this invention are used in in situ hybridization (ISH) and fluorescence in situ hybridization (FISH) assays. Excess probe used in an ISH or FISH assay typically must be removed so that the detectable moiety of the specifically bound probe can be detected above the background signal that results from still present but unhybridized probe. Generally, the excess probe is washed away after the sample has been incubated with probe for a period of time. However, the use of self-indicating probes is a preferred embodiment of this invention, since there is no requirement that excess self-indicating probe be completely removed (washed away) from the sample since it generates little or no detectable background. In addition to ISH or FISH assays, self-indicating probes comprising the selected probing nucleobase sequence described herein are particularly useful in all kinds of homogeneous assays such as in real-time PCR or useful with self-indicating devices (e.g. lateral flow assay) or self-indicating arrays.

EXAMPLES

This invention is now illustrated by the following examples, which are not intended to be limiting in any way.

Example 1

PNA probe sequence
Fluconazole Sensitive Probe Set
Probe A-Fam
Fam-OO-AGAGAGCAGCATGCA-NH$_2$ (Seq. Id. No. 1)

Fluconazole Resistant Probe Set
Probe B-Tam
Tam-OO-GCAAGGGGCGCAAA-NH$_2$ (Seq. Id. No. 2)

Probe F-Tam
Tam-OO-GCAGCGGTGCGCAA-NH$_2$ (Seq. Id. No. 6)
(Note: Conventional nomenclature used to illustrate the termini of the PNA probe; O = 8-amino-3,6-dioxaoctanoic acid; Fam = 5(6)-carboxyfluorescein, Tam = 5(6)-carboxytetramethyrhodamine.)

Strains

Overnight cultures of reference strains were prepared representing various *Candida* species including *C. albicans*, *C. glabrata*, *C. guillermondii*, *C. kefyr*, *C. krusei*, *C. lusitaniae*, *C. parapsilosis*, *C. tropicalis*, as well as baker's yeast, *S. cerevisiae*, and *Staphylococcus epidermidis*, a frequent blood culture contaminant.

Preparation of Smears

For each strain, smears were prepared on a 8-mm diameter well of a Teflon-coated microscope slide (AdvanDx, Woburn, Mass.) by mixing one drop of culture with one drop of phosphate-buffered saline containing 1% (v/v) Triton X-100. The slide was then placed on a, 55° C. slide warmer for 20 min at which point the smears were dry. Subsequently, the smears were disinfected by immersion into 96% (v/v) ethanol for 5-10 minutes and air-dried.

Fluorescence in situ hybridization (FISH).

Smears were covered with a drop of hybridization solution containing 10% (w/v) dextran sulfate, 10 mM NaCl, 30% (v/v) formamide, 0.1% (w/v) sodium pyrophosphate, 0.2% (w/v) polyvinylpyrrolidone, 0.2% (w/v) ficoll, 5 mM Na$_2$EDTA, 1% (v/v) Triton X-100, 50 mM Tris/HCl pH 7.5 and 250 nM Probe A-Fam, 25 nM Probe B-Tam and 25 nM Probe F-Tam. Coverslips were placed on the smears to ensure even coverage with hybridization solution, and the slides were subsequently placed on a slide warmer (Slidemoat, Boekel, Germany) and incubated for 90 min at 55° C. Following hybridization, the coverslips were removed by submerging the slides into approximately 20 ml/slide prewarmed 25 mM Tris, pH 10, 137 mM NaCl, 3 mM KCl in a water bath at 55° C. and washed for 30 min. Each smear was finally mounted using one drop of Mounting medium (AdvanDx, Woburn, Mass.) and covered with a coverslip. Microscopic examination was conducted using a fluorescence microscope equipped with a FITC/Texas Red dual band filter set. Fluconazole sensitive fungi were identified by green fluorescent buds and Fluconazole resistant fungi were identified by red fluorescent buds. Results are recorded in Table 2.

TABLE 2

| Species Id. | Result | Incidence[1] |
|---|---|---|
| C. albicans | Positive/Green (Fluconazole Sensitive) | 54.5% |
| C. glabrata | Positive/Red (/Fluconazole Resistant) | 12.3% |
| C. krusei | Positive/Red (/Fluconazole Resistant) | 1.5% |
| C. parapsilosis | Negative | 17.8% |
| C. tropicalis | Negative | 9.5% |
| Other Candida spp.[2] | Negative | 4.5% |
| S. cerevisiae | Negative | N/A |
| S. epidermidis | Negative | N/A |

[1]Average incidence of Candida species for the United States, Europe, Canada, and Latin America. M. A. Pfaller et al. International Surveillance of Bloodstream Infections Due to Candida Species: Frequency of Occurrence and In Vitro Susceptibilities to Fluconazole, Ravuconazole, and Voriconazole of Isolates Collected from 1997 through 1999 in the SENTRY Antimicrobial Surveillance Program. JCM. Vol. 39, No. 9. p. 3254-3259. September 2001.
[2]Candida spp. was represented by C. guillermondii, C. kefyr, and C. lusitaniae which all have low prevalence in the clinical setting.
N/A: Not applicable (Non-Candida species used as controls)

With reference to Table 2, the table displays species identification in the left column, PNA FISH results in the center column, and clinical incidence of the species in the right column. With reference to Table 2, three of the species tested gave a positive result, the C. albicans sample contained green fluorescent buds, and the C. glabrata and C. krusei samples contained red fluorescent buds. The C. parapsilosis slide had cells which displayed a weak yellow fluorescence which was scored negative. The positive results demonstrate that the probe mixture tested produces green signals, indicating fluconazole sensitivity, with C. albicans and red signals, indicating fluconazole resistance, with either C. glabrata or C. krusei. Though only three species are detected with this assay, the species detected represent nearly 70% of the Candida seen clinically in the United States, Europe, Canada, and Latin America.

This probe mixture and technique would be useful for selection of therapy since a green signal indicates a species (C. albicans) which is generally regarded as fluconazole sensitive, whereas a red signal indicates species (C. glabrata or C. krusei) which are often or likely fluconazole resistant.

Example 2

Example 2 was performed exactly as Example 1, except that a second probe was added to the Fluconazole Sensitive probe set.

```
PNA probe sequence
Fluconazole Sensitive Probe Set
Probe A-Fam
Fam-OO-AGAGAGCAGCATGCA-NH2        (Seq. Id. No. 1)

Probe I-Fam
Fam-OO-GAGAGTAACATACAA-NH2        (Seq. Id. No. 9)

Fluconazole Resistant Probe Set
Probe B-Tam
Tam-OO-GCAAGGGGCGCAAA-NH2         (Seq. Id. No. 2)

Probe F-Tam
Tam-OO-GCAGCGGTGCGCAA-NH2         (Seq. Id. No. 6)
(Note: Conventional nomenclature used to illus-
trate the termini of the PNA probe; O = 8-amino-
3,6-dioxaoctanoic acid; Fam = 5(6)-carboxyfluores-
cein, Tam = 5(6)-carboxytetramethyrhodamine.)
```

Probe-I-Fam was added in the hybridization solution at 500 nM, along with the other probes as described in Example 1. Microscopic examination was conducted using a fluorescence microscope equipped with a FITC/Texas Red dual band filter set. Fluconazole Sensitive fungi were identified by green fluorescent buds and Fluconazole Resistant fungi were identified by red fluorescent buds. Results are recorded in Table 3.

TABLE 3

| Species Id. | Result | Incidence[1] |
|---|---|---|
| C. albicans | Positive/Green (Fluconazole Sensitive) | 54.5% |
| C. glabrata | Positive/Red (/Fluconazole Resistant) | 12.3% |
| C. krusei | Positive/Red (/Fluconazole Resistant) | 1.5% |
| C. parapsilosis | Positive/Green (Fluconazole Sensitive) | 17.8% |
| C. tropicalis | Negative | 9.5% |
| Other Candida spp.[2] | Negative | 4.5% |
| S. cerevisiae | Negative | N/A |
| S. epidermidis | Negative | N/A |

[1]Average incidence of Candida species for the United States, Europe, Canada, and Latin America. M. A. Pfaller et al. International Surveillance of Bloodstream Infections Due to Candida Species: Frequency of Occurrence and In Vitro Susceptibilities to Fluconazole, Ravuconazole, and Voriconazole of Isolates Collected from 1997 through 1999 in the SENTRY Antimicrobial Surveillance Program. JCM. Vol. 39, No. 9. p. 3254-3259. September 2001.
[2]Candida spp. was represented by C. guillermondii, C. kefyr, and C. lusitaniae which all have low prevalence in the clinical setting.

With reference to Table 3, the table displays species identification in the left column, PNA FISH results in the center column, and clinical incidence of the species in the right column. With reference to Table 3, only four of the species tested gave a positive result. The C. albicans and C. parapsilosis samples contained green fluorescent buds, and the C. glabrata and C. krusei samples contained red fluorescent buds. The positive results demonstrate that the probe mixture tested produces signals of green, for Fluconazole Sensitive, with C. albicans and C. parapsilosis, and red, for Fluconazole Resistant, with either C. glabrata or C. krusei. Though only four species are detected with this assay, those species represent over 86% of the blood stream infections caused by Candida species in the United States, Europe, Canada, and Latin America.

This probe mixture and technique would be useful for selection of therapy since a green signal indicates species (C. albicans and C. parapsilosis) which are generally regarded as fluconazole sensitive, whereas a red signal indicates species (C. glabrata or C. krusei) which are often or likely fluconazole resistant. Neither of the fluorescent signal types (red or green) in this assay positively identifies organisms to a species level; they indicate fluconazole susceptibility-types.

C. tropicalis is an example of the "susceptible/dose-dependant" susceptibility-type for fluconazole. Though not detected in this example, a prospective probe set of a third color specific to the fluconazole susceptible/dose-dependant susceptibility-type can be envisioned, for example, a probe set containing Probe-N. Addition of a prospective third probe set for detection of this susceptibility-type, including C. tropicalis, could account for greater than 96% of the blood stream infections caused by Candida species in the United States, Europe, Canada, and Latin America.

Example 3

Example 3 was performed exactly as Example 1, but with a different probe set.

```
PNA probe sequence
Fluconazole Intermediate Probe Set
Probe N-Tam
Tam-OO-AAGAAGTAACATACA-NH2   (Seq. Id. No. 14)
(Note: Conventional nomenclature used to
illustrate the termini of the PNA probe;
O = 8-amino-3,6-dioxaoctanoic acid; Tam =
5(6)-carboxytetramethyrhodamine.)
```

Probe N-Tam was added in the hybridization solution at 250 nM. Microscopic examination was conducted using a fluorescence microscope equipped with a FITC/Texas Red dual band filter set. Fluconazole Intermediate fungi were identified by red fluorescent buds. Results are recorded in Table 4.

TABLE 4

| Species Id. | Result | Incidence[1] |
| --- | --- | --- |
| C. albicans | Negative | 54.5% |
| C. glabrata | Negative | 12.3% |
| C. krusei | Negative | 1.5% |
| C. parapsilosis | Negative | 17.8% |
| C. tropicalis | Positive/Red (Fluconazole Intermediate) | 9.5% |
| Other Candida spp.[2] | Negative | 4.5% |
| S. epidermidis | Negative | N/A |

[1]Average incidence of Candida species for the United States, Europe, Canada, and Latin America. M. A. Pfaller et al. International Surveillance of Bloodstream Infections Due to Candida Species: Frequency of Occurrence and In Vitro Susceptibilities to Fluconazole, Ravuconazole, and Voriconazole of Isolates Collected from 1997 through 1999 in the SENTRY Antimicrobial Surveillance Program. JCM. Vol. 39, No. 9. p. 3254-3259. September 2001.
[2]Candida spp. was represented by C. guilliermondii, C. kefyr, and C. lusitaniae which all have low prevalence in the clinical setting.
N/A: Not applicable (Non-Candida species used as controls)

With reference to Table 4, the table displays species identification in the left column, PNA FISH results in the center column, and clinical incidence of the species in the right column. With reference to Table 4, only one of the species tested gave a positive result. The C. tropicalis sample contained red fluorescent buds. The positive results demonstrate that the probe mixture tested produces red signal, for Fluconazole Intermediate, only with C. tropicalis cells.

This probe mixture and technique would be useful for selection of therapy since a red signal indicates a species (C. tropicalis) which is fluconazole intermediate.

Though C. tropicalis is isolated from patients in only ~10% of BSI caused by fungi, there is clinical value in the ability to rapidly identify the infection as one which is likely sensitive to high doses of fluconazole.

Example 4

Example 4 was performed exactly as Example 1, but with a different probe set.

```
PNA probe sequence
Caspofungin Susceptible/Dose Dependant Probe Set
Probe S-Fam
Fam-OO-CCTTCCACACAGACTC-NH2        (Seq. Id. No. 19)

Probe T-Fam
Fam-OO-TAGGTCTGGGACATC-NH2         (Seq. Id. No. 20)
(Note: Conventional nomenclature used to illus-
trate the termini of the PNA probe; O = 8-amino-
3,6-dioxaoctanoic acid; Fam = 5(6)-carboxyfluores-
cein).
```

Probes S-Flu and T-Flu were added in the hybridization solution at 100 nM each. Microscopic examination was conducted using a fluorescence microscope equipped with a FITC/Texas Red dual band filter set. Caspofungin Susceptible/Dose Dependant (S/DD) fungi were identified by green fluorescent buds. Results are recorded in Table 5.

TABLE 5

| Species Id. | Result | Incidence[1] |
| --- | --- | --- |
| C. albicans | Negative | 54.5% |
| C. glabrata | Negative | 12.3% |
| C. krusei | Positive/Green (Caspofungin S/DD[3]) | 1.5% |
| C. parapsilosis | Positive/Green (Caspofungin S/DD[3]) | 17.8% |

TABLE 5-continued

| Species Id. | Result | Incidence[1] |
| --- | --- | --- |
| C. tropicalis | Negative | 9.5% |
| Other Candida spp.[2] | Negative | 4.5% |
| S. epidermidis | Negative | N/A |

[1]Average incidence of Candida species for the United States, Europe, Canada, and Latin America. M. A. Pfaller et al. International Surveillance of Bloodstream Infections Due to Candida Species: Frequency of Occurrence and In Vitro Susceptibilities to Fluconazole, Ravuconazole, and Voriconazole of Isolates Collected from 1997 through 1999 in the SENTRY Antimicrobial Surveillance Program. JCM. Vol. 39, No. 9. p. 3254-3259. September 2001.
[2]Candida spp. was represented by C. guilliermondii, C. kefyr, and C. lusitaniae which all have low prevalence in the clinical setting.
N/A: Not applicable (Non-Candida species used as controls)
[3]In Pfaller, et al. (J Clin Microbiol. 2006 Mar; 44(3): 760-3) species were grouped as "most" susceptible to caspofungin that had $MIC_{90}$ values between 0.03 and 0.06 ug/ml, and "significantly less" susceptible to caspofungin that had $MIC_{90}$ values ≥0.5 ug/ml. Here we interpret "significantly less" susceptibility as susceptible/dose dependant.

With reference to Table 5, the table displays species identification in the left column, PNA FISH results in the center column, and clinical incidence of the species in the right column. With reference to Table 5, only two of the species tested gave a positive result. The C. parapsilosis and C. krusei samples contained green fluorescent buds. The positive results demonstrate that the probe mixture tested produces green signal, for caspofungin Susceptible/Dose Dependant, only with C. parapsilosis and C. krusei cells.

This probe mixture and technique would be useful for selection of therapy since a green signal indicates two species (C. parapsilosis and C. krusei) which require increased dosage of caspofungin. Though C. parapsilosis and C. krusei are isolated from patients in only ~19.3% (17.8%+1.5%) of BSI caused by fungi, there is clinical value in the ability to rapidly identify the infection as one which is likely to require higher doses of caspofungin.

Example 5

Example 5 is performed exactly as Example 4, but with an expanded probe set.

```
PNA probe sequence
Expanded Caspofungin Susceptible/Dose Dependant
Probe Set
Probe S-Fam
Fam-OO-CCTTCCACACAGAGTC-NH2        (Seq. Id. No. 19)

Probe T-Fam
Fam-OO-TAGGTCTGGGACATC-NH2         (Seq. Id. No. 20)

Probe W-Fam
Fam-OO-GCATCAACGCAGGCT-NH2         (Seq. Id. No. 23)

Probe X-Fam
Fam-OO-GACTCAGACCACGA-NH2          (Seq. Id. No. 24)
(Note: Conventional nomenclature used to illus-
trate the termini of the PNA probe; O = 8-amino-
3,6-dioxaoctanoic acids; Fam = 5(6)-carboxy-
fluorescein)
```

All probes are added in the hybridization solution at 100 nM each. Probe W is designed to specifically detect Candida guilliermondii (anamorph of Pichia guilliermondii), and Probe X is designed to specifically detect Candida lusitaniae (also called Clavispora lusitaniae). Though both of these species are relatively rare in clinical samples, they also require increased dosage of caspofungin ($MIC_{90}$ values ≥0.5 ug/ml). Use of the Expanded Caspofungin Susceptible/Dose Dependant Probe Set as described here would allow detection of four species which typically require increased caspofungin dosage with a single probe set. This probe mixture and technique would be useful for selection of therapy since a green signal should indicate any of four species (*C. parapsilosis, C. krusei, C. guilliermondii*, and *C. lusitaniae*) which require increased dosage of caspofungin.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

The disclosures of all references mentioned herein are incorporated by reference in their entirety for all purposes.

What is claimed is:

1. A peptide nucleic acid (PNA) probe consisting of the nucleic acid sequence of SEQ ID NO: 17.

2. A reagent for classification of fungi comprising the peptide nucleic acid (PNA) probe consisting of SEQ ID NO:17 and optionally at least one detectable moiety, wherein the reagent is used to determine at least one fungal drug susceptibility-type.

3. The reagent of claim 2, further comprising one or more additional probes complementary to nucleic acid sequences corresponding to other fungi of other drug susceptibility-types.

4. The reagent of claim 2, wherein a fungal drug-susceptibility type comprises a full spectrum of response to a compound, wherein the full spectrum of response comprises one or more of susceptible; susceptible/intermediate; intermediate; susceptible/susceptible, dose-dependent; susceptible, dose-dependent; susceptible, dose-dependent/resistant; susceptible-dose/delivery dependent; intermediately resistant; or resistant.

5. The reagent of claim 2, wherein the fungal drug susceptibility-type comprises resistance to an anti-fungal compound, or combination of compounds.

6. The reagent of claim 5, wherein the anti-fungal compound comprises fluconazole.

7. The reagent of claim 2, wherein at least one fungal drug susceptibility type is a fluconazole-resistant drug susceptibility-type.

8. The reagent of claim 7, wherein the fluconazole-resistant drug susceptibility-type comprises one or more of *Candida glabrata*.

9. The reagent of claim 2, wherein the PNA probe has at least one detectable moiety.

10. The reagent of claim 9, wherein the detectable moiety or moieties comprise one or more of a conjugate, a branched detection system, a chromophore, a fluorophore, a spin label, a radioisotope, an enzyme, a hapten, an acridinium ester or a luminescent compound.

11. The reagent of claim 10, wherein coincidental fluorescence is used to detect a fungal susceptibility-type.

12. A kit for selecting antifungal therapy, comprising the peptide nucleic acid (PNA) probe consisting of SEQ ID NO:17 and optionally at least one detectable moiety and instructions for use.

* * * * *